United States Patent [19]

Bernard et al.

[11] Patent Number: 5,039,793

[45] Date of Patent: Aug. 13, 1991

[54] CYTOPLASMIC PROTEIN OF SUPRABASAL EPIDERMAL CELLS, ANTIBODIES CAPABLE OF RECOGNIZING SAID PROTEIN, AND HYBRID CELLULAR STOCKS CAPABLE OF SECRETING SUCH ANTIBODIES

[75] Inventors: Bruno Bernard; Yves M. Darmon, both of Antibes, France

[73] Assignee: Centre International De Recherches Dermatologiques, Valbonne, France

[21] Appl. No.: 114,945

[22] Filed: Oct. 30, 1987

[30] Foreign Application Priority Data

Oct. 31, 1986 [FR] France ................... 8615207

[51] Int. Cl.$^5$ ................... C07K 15/06; C07K 15/28; C12P 21/08; C12N 5/20
[52] U.S. Cl. ................... 530/350; 530/387; 435/70.21; 435/240.27; 935/104
[58] Field of Search ............... 530/350, 387; 436/548, 436/518; 435/240.27, 70.21, 948, 7, 172.2; 935/89, 95, 104, 108, 110

[56] References Cited

FOREIGN PATENT DOCUMENTS 0157613 11/1985 European Pat. Off. .
0163303 12/1985 European Pat. Off. .
0163304 12/1985 European Pat. Off. .
8503132 7/1985 PCT Int'l Appl. .

OTHER PUBLICATIONS

Stedman's Medical Dictionary 24th Edition, 1982 Williams & Wilkins.
Proc. Natl. Acad. Sci. USA, vol. 83; No. 8, Apr. 1986, pp. 2657–2661, Parrish et al.: "Mouse antisera specific for desmosomal adhesion molecules of suprabasal skin cells, meninges, meningioma".
Chemical Abstracts, vol. 100; No. 21, May 1984; page 453, No. 172635k, Weiss et al.
Biological Abstracts, vol. 78; No. 8, Aug. 1984, No. 60667, Murphy et al.: "Involucrin expression in normal and neoplastic human skin: A marker for kerationocyte differentiation".
Cancer Research, vol. er, Feb. 1985; pp. 783–790, Hamburger et al: "Isolation and characterization of a monoclonal antibody specific for epithelial cells".
Biological Abstracts, vol. 80, No. 1, Jul. 1985, No. 4165, Viac et al.: "A monoclonal antibody labeling the keratinocyte membrane: A marker of epidermal differentiation".
Proc. Natl. Acad. Sci. U.S.A., vol. 83; No. 19, Oct. 1986, pp. 7282–7286, Jones et al.: "A cell surface desmosome-associated component: Identification of a tissue-specific cell adhesion molecule".
Chemical Abstracts, vol. 105, No. 11; Sep. 1986, page 480, No. 95671t, Bernard.
Chemical Abstracts, vol. 105; No. 7, Aug. 1986, page 411, No. 58395k, King et al.
Chemical Abstracts, vol. 105; No. 7, Aug. 1986, page 438, No. 58657x, Ma et al.

Primary Examiner—Margaret Moskowitz
Assistant Examiner—Hazel F. Sidberry
Attorney, Agent, or Firm—Cushman, Darby & Cushman

[57] ABSTRACT

A protein characterized by the fact that it is a nonkeratinic protein present in the cytoplasm of suprabasal epidermal cells, in particular in man, and absent in basocellular carcinoma, melanoma and naevus cells; antibodies directed against said protein, their preparation and their application as reagents; cellular stocks secreting such antibodies, and their preparation.

7 Claims, No Drawings

CYTOPLASMIC PROTEIN OF SUPRABASAL EPIDERMAL CELLS, ANTIBODIES CAPABLE OF RECOGNIZING SAID PROTEIN, AND HYBRID CELLULAR STOCKS CAPABLE OF SECRETING SUCH ANTIBODIES

The present invention relates to a protein present in the cytoplasm of suprabasal cells of the normal human epidermis, and to monoclonal and polyclonal antibodies, which reconize an antigen site of said protein, to their preparation and to their use, in particular, as reagents for the study of the normal or pathological differentiation of the cells of the epidermis.

It is known that the epidermis contains a basal membrane on which rests a layer of proliferative basal cells and suprabasal layers of cells in the process of differentiation which are progressively keratinized and finished by forming on the surface of the skin a corneal layer of completely keratinized dead cells. All these cells are constantly renewed from the proliferative basal layer.

In order to study skin diseases (for example, psoriasis, warts, papilloma, cancers, etc.), it is necessary to have a better understanding of the differentiation between normal and malignant epidermal cells, which are further called keratinocytes.

For example, it is not presently known if psoriasis is caused by an excessive proliferation of cells of the basal membrane, such as the cells which did not have time to be differentiated (in other words, the differentiation stopped at a certain stage) or indeed if it is caused by a differentiation of diseased cells other than that of the normal cells.

In order to carry out such studies, it is important to have different markers for the differentiation of the keratinocytes.

The present invention relates to such markers, to their preparation and to their use.

In particular, the present invention relates to a new protein, characterized by the fact:

that it is a nonkeratinic protein present in the cytoplasm of epidermal suprabasal cells, in particular in man, monkey, horse, cow, mouse and guinea pig, and to a lesser degree, in goat;

that it is absent in the following epithelial tissues of man: ureter, stomach, colon and small intestine, but is present in the esophagus;

that it is absent in the following pathological cells: basal cell carcinoma, melanoma and naevus;

that it is decreased or absent in the following pathological cells: spinocellular carcinoma, psoriasis, papilloma; and that it is immunologically bound by the antibody secreted by the hybrid cellular stock BC5 deposited on Oct. 27, 1986 in the National Collection of Microorganisms of the Pasteur Institute 25 rue du Docteur Roux, 75724 Paris Ceder 15, France, under the No. I-615 in accordance with the provisions of the European convention regulations, according to rules 28 and 28 bis;

as well as the analogs of said protein, said analogs being all synthetic or semi-synthetic fragments and peptides containing peptide sequences present on said protein, as well as all derivatives of said fragments or peptides, provided that said fragments, peptides or derivatives are recognized by the previously defined antibody.

The present invention also relates to a protein such as defined above whose molecular weight, measured by electrophoresis on polyacrylamide gel, is 62,000 daltons.

The protein of the present invention has been isolated and characterized in the manner which will be described below, by preparation of hybrid cells that secrete antibodies which are characteristic of epidermal suprabasal cells.

This protein is prepared by a method principally characterized by the fact that keratinocytes are used as starting materials and, in particular, transformed human keratinocytes which can be cultivated in vitro; that a lysis of the cells is carried out with a suitable detergent, and that said protein is isolated in accordance with known methods for the purification of proteins, for example a method comprising a step of affinity chromatography on a chromatographic support carried out with a monoclonal antibody, such as described below.

The present invention also relates to antibodies that recognize an antigenic determinant of a protein defined above. These antibodies are either monoclonal antibodies or polyclonal antibodies which are purified, for example, by immunoadsorption on the protein. The invention, of course, covers the corresponding Fab or F(ab')$_2$ fragments which are obtained by enzyme cleaving.

Among the monoclonal antibodies of the invention, those which are secreted by the hybrid cellular stock mentioned above can be cited in particular.

The present invention also relates to antibodies, as defined above, modified by being labelled with a radioactive, fluorescent or enzymatic tracer, obtained in accordance with conventional methods for preparing such labelled antibodies.

For example, the tracer can be a radioactive tracer obtained by isotopic exchange with a radioactive isotope of iodine or indium.

The coupling of the antibodies with a fluorochrome (for example fluorescein or rhodamine isothiocyanate) or with an enzyme is also known. The enzyme is, for example, a peroxydase or an alkaline phosphatase. The enzyme activity possibly present on the reagent, after carrying out a test, can be determined using known methods with a suitable substrate providing, for example, an indication using colorimetry, fluorescence, luminescence, potentiometry, etc.

The present invention also relates to monoclonal antibodies obtained in accordance with the known technique of hybridomas starting from lymphocytes removed from immunized animals, using conventional methods, with the protein defined above.

The present invention further relates to antibodies, as defined above, labelled or not, fixed on a solid support enabling their use as immunoadsorbent agents in methods using affinity chromatography or as reagents in the methods of analysis based on the antigen-antibody reaction (radioimmunological techniques, immunofluorescence techniques, and immunoenzymatic techniques).

This solid support can be prepared with any solid, biological or synthetic material, having adsorbent properties or capable of fixing a coupling agent. These materials are known and described in the literature. Representative solid materials, capable of fixing the antibodies by adsorption include, for instance, polystyrene, polypropylene, latex, etc. Representative solid materials which can be used to fix the antibodies by covalence using a coupling agent include, for instance, dextran, cellulose, their amine derivatives (diethylaminoethyl cellulose or diethylaminoethyl dextran), etc.

The solid support can, for example, be in the form of discs, tubes, rods, bearings or microtitration plates.

The coupling agents enabling the antibodies to be fixed by covalence onto the solid support are bifunctional derivatives such as dialdehydes, quinones, etc.

The antibodies can also be fixed in a known manner onto solid mineral supports.

In order to prepare the monoclonal antibodies, hybrid cells are prepared in advance, and a further object of the present invention is a method for the preparation of hybrid cells that secrete an antibody as defined above, wherein an animal is immunized with the protein defined above or with keratinocytes, in particular human keratinocytes; the lymphocytes of the immunized animal are removed, using known methods; a cellular fusion is carried out with lymphocytes which can be cultivated in vitro; and a selection is made of the clones secreting antibodies that recognize an antigen which is characteristic of the cytoplasm of the suprabasal epidermal cells of man and other mammals, such as those enumerated above. The keratinocyte used as the starting material is, in particular, a keratinocyte transformed by the SV40 virus for example.

The present invention also relates to a method for the preparation of monoclonal antibodies by culture of the hybrid cellular stocks described above and separation of the antibodies produced in the culture medium or even in the ascites.

If desired, said antibodies are fixed on a support using known methods and/or are reacted with a radioactive, fluorescent or enzymatic marker in accordance with known methods.

The present invention further relates to the use of the monoclonal antibodies, such as are defined above, as reagents in techniques based on the antigen-antibody reaction.

These techniques, such as direct or indirect immunofluorescence, immunoenzymatic techniques, radioimmunological techniques, etc., are known and are not described herein.

The antibodies of the present invention can be used, in particular, as reagents for the study of the normal or pathological differentiation of epidermal cells. They can, in particular, be used in the diagnosis of dermatological diseases and also of diseases of the internal epithelia.

They can be used in all medical imaging techniques using antibodies.

In addition, the antibodies of the present invention, fixed on an appropriate solid support, can be used in the preparation of reagents for affinity chromatography.

The following nonlimiting examples are given to illustrate the present invention.

EXAMPLE 1 - Obtaining Monoclonal Antibodies

1) Culture of SV-K14 Cells

The stock of transformed human keratinocytes using the SV40 virus and called SV-K14 was employed (Taylor-Papadimitriou et al, Cell Diff. 11, 169, 1982). This cell stock was deposited with ICRF (Imperial Cancer Research Fund, P.O. Box 123, Lincoln's Inn Fields, London WC2A3PX, U.K.).

The cells of this stock were cultured in an Eagle medium modified with Dulbecco containing 4.5 g/l of glucose and 1.2 g/l of sodium bicarbonate added to 10% calf fetal serum in a damp incubator containing 5% $CO_2$–95% air at 37° C. Appropriate tests enabled a check on the absence of mycoplasms in these cultures. Recent studies (Bernard et al, Cancer Res. 45, 1707, 1985) enabled it to be demonstrated that the SVK14 cells possess many characteristics of basal keratinocytes and are only capable of limited differentiation.

2) Immunization

Female BALB/c mice aged 8 to 12 weeks were immunized intraperitoneally with $2 \times 10^7$ SVK14 cells. This was repeated identically 3 weeks later. The animals' spleens were removed exactly 3 days after the second treatment.

3) Culture of SP2/O Mouse Myeloma Cells

A stock of SP2/O cells (Shulman and Köhler, Nature 276, 269, 1978) was used which are incapable of survival in a medium containing azaserine and hypoxanthine (Buttin et al, Curr. Top. Microbiol. Immunol. 81, 27, 1978). The cells were cultured in an Eagle medium modified with Dulbecco (DME) containing 4.5 g/l of glucose, 1.2 g/l of sodium bicarbonate, 1 mM of sodium pyruvate, 2 mM of glutamine, 100 U of penicillin/ml, 1 $\mu$g of streptomycin/ml, (which is a complete DME medium) added to 10% decomplemented calf fetal serum (30 minutes at 56° C.). After thawing, the SP2/O cells had to be cultured at concentrations from $2 \times 10^4$ to $5 \times 10^5$/ml until they doubled in a time of from 12 to 15 hours. The efficiency of cloning was determined by limit dilution and should be close to 100%. The freezing of these cells was carried out at a concentration of from $5 \times 10^6$ to $10^7$ ml in 95% calf fetal serum and 5% DMSO.

4) Preparation of SP2/O Cells

SP2/O cells in exponential growth at a concentration of $10^5$ to $2 \times 10^5$ cells per ml were centrifuged at 800 rpm for 5 minutes and resuspended in complete DME without serum at a density of $10^7$ cells/ml.

To carry out a fusing, $10^7$ myeloma cells are necessary.

5) Preparation of Splenocytes

The splenocytes of the immunized mice were prepared in a conventional manner and were placed in suspension in a complete DMEM (Dulbecco's Modified Essential Medium) medium without serum. For counting, 50 $\mu$l of the suspension were removed and mixed with 50 $\mu$l of 0.2% trypan blue and 400 $\mu$l of PBS (phosphate buffered saline). After 30 seconds, an aliquot was placed in a Buerker cell; the total number of splenocytes of a spleen was $10^8$ to $1.6 \times 10^8$. The percentage of dead cells was less that 20%. The suspension was centrifuged at 800 rpm for 5 minutes and adjusted to $10^8$ viable cells/ml.

6) Fusion (Day 0)

The technique used is derived form the technique of "fusion en masse" of Juy et al (J. Immunol. 129, 1153, 1982).

In a 50 ml polypropylene tube, $10^7$ myeloma cells (1 ml) and $4 \times 10^7$ splenocytes (0.4 ml) were mixed and centrifuged at 800 rpm (rotations per minute) for 5 minutes. The supernatant was pipetted and 1 drop of complete DME was added without serum to the deposit which was then replaced in suspension (Galfre et al, Nature 266, 550, 1977). 400 $\mu$l of polyethylene glycol 1000 (PEG 1000) at 45% in the DME was added dropwise to the deposit over 30 seconds by slowly shaking the tube from time to time. It was left to react for 3 minutes at room temperature by slowly shaking from time to time. 1 ml of complete DME containing 10% of calf fetal serum (SFV) was then added over 5 minutes (approximately 1 drop every 2 seconds); the tube was inclined and lightly shaken. After these 5 minutes, 10 to 15 ml of complete medium containing calf fetal serum were rapidly added dropwise without shaking. This suspension was removed with a 10 ml pipette and distributed in a culture dish with a 100 mm diameter which was incubated in an incubator at 37° C. for 2 to 3 hours. Then the volume of the suspension was adjusted to 40 ml. The suspension was then distributed into the cups of culture plates with 24 holes at a rate of 0.4 ml/cup. 4 fusion plates were prepared.

7) Day 1

0.4 ml/cup of selective medium complete DME medium with SFV containing $5 \times 10^{-5}$M hypoxantine and $10^{-5}$M azaserine were added.

8) Day 3

The operation of day 1 was repeated.

Under these conditions, hybridoma clones appeared between day 6 and day 9.

9) Labelling The Clones Producing The Desired Antibodies

When the clones covered one-third of the surface of the cups and/or the medium became an orange yellow, the supernatant was tested using indirect immunofluorescence on SVK14 cultures and on epidermal sections in accordance with the techniques described by Bernard et al (Cancer Res. 45, 1707, 1985) and Bernard et al (Brit. J. Dermatol. 112, 617, 1985).

10) Transplanting Selected Cups

Before the cups were half full, they were transplanted into 3 other cups in total. At this stage were carried out, on the one hand, a freezing and, on the other hand, a subcloning into plates with 96 holes (1 row with 10 cells/cup, 1 row with 5 cells/cup, 2 rows with 2 cells/cup, 2 rows with 1 cell/cup, 2 rows with 0.5 cell/cup). For the subcloning a plate containing a medium composed of 10 to 50% of macrophage supernatant could also be prepared. The supernatants of the positive cups were tested using indirect immunofluorescence. Two positive clones were then cultured.

One of the two clones ($BC_5$) was deposited in the National Collection of the Pasteur Institute, under the number previously indicated.

11) Growth in Ascite

The growth of a hybridoma in ascite liquid was obtained after intraperitoneal injection of $10^7$ cells from a same clone to BALB/c mice aged 8 weeks which had been previously sensitized by intraperitoneal injection of 0.5 ml of pirstane (pristane is 2,6,10,14-tetramethyl pentadecane).

12) Identification of the Class and Subclass of Secreted Immunoglobulins

The class of the immunoglobulins secreted in the myeloma supernatant was determined by double diffusion in agar with specific reagents of the heavy chains of immunoglobulins (Serotec Ltd., Bicester, Great Britain).

The immunoglobulin secreted by the $BC_5$ clone was an IgM.

Example 2 - Identification of Recognized Antigens

1) SVK14 Cell

Studies carried out using indirect immunofluorescence have shown that the immunoglobulin secreted by the $BC_5$ cell enabled considerable labelling of the unfixed SVK14 cells, of those fixed with formaldehyde, and those fixed with formaldehyde in the presence of Triton X-100 (isooctylphenol polyethyloxylated with 10 moles of ethylene oxide).

2) Immunoprecipitation

The SVK14 cells were metabolically labelled for 24 hours at 37° C. with $^{35}$S-methionine or 2-$^3$H-mannose, in a complete culture medium. The medium contained 150 $\mu$Ci of $^{35}$S-methionine (New England Nuclear; 400 Ci/mmol) for 100 $\mu$Ci of 2-$^3$H-mannose (New England Nuclear; 20 Ci/mmol) per ml. After washing with PBS, the cells were lysed on ice and for 30 minutes in an extraction buffer composed of PBS without $Ca^{++}$ nor $Mg^{++}$, containing 1% of Triton X-100, 0.5% of sodium deoxycholate, 0.1% of sodium dodecylsulfate and 0.2% of $NaN_3$. This buffer further contained 25 $\mu$l of DNAse I (at 2 mg/ml) and 5 $\mu$l RNAse A (at 5 mg/ml). 10 ml of lysis buffer were necessary to lyse 175 $cm^2$ of cultures. The supernatants were collected and clarified by centrifugation at 15,000 g for 30 minutes at 4° C. The immunoprecipitation was carried out by incubating 500 $\mu$l of cellular extract with 3 $\mu$l of supernatant from the hybridoma culture medium for 16 hours at 4° C. Then, 50 $\mu$l of rabbit immunoglobulins mouse anti-immunoglobulin (Cappel Laboratories, Cochranville, PA, USA) were added and the incubation was extended for 2 hours at 4° C. The immune complexes were then isolated by adding 150 $\mu$l of A-Sepharose protein (Pharmacia Fine Chemicals, Uppsala, Sweden) diluted in 500 $\mu$l of lysis buffer, incubating it while stirring for 2 hours at 20° C. and centrifuging it at 13,000 g for 10 minutes. After 3 washes in the lysis buffer, the deposit was extracted at 100° C. in the presence of 1% sodium dodecylsulfate (SDS) at 5% beta-mercaptoethanol and analyzed by electrophoresis in polyacrylamide-SDS gel using the method of Laemmli (Laemmli, Nature, 227, 680, 1970).

In this manner, the protein of the invention was obtained which had the characteristics mentioned above.

3) Immunodetection After Electrotransfer of Proteins

The technique used is similar to that described by Bernard et al (Cancer Research 45, 1707, 1985). The SVK14 cells were lysed in PBS containing 1% sodium dodecylsulfate and 5% beta mercaptoethanol. After scratching the culture dishes, the extracts were clarified by sonication and heated to 100° C. for 5 minutes. The cellular proteins (60 $\mu$g in 20 $\mu$l) were then separated by electrophoresis in polyacrylamide-SDS gel and transferred onto nitrocellulose using the method of Towbin et al (Proc. Natl. Acad. Sci. USA 76, 4350, 1979). The reactive protein bands (that is reacting with the antibody) were then shown by the technique of coloration using peroxydase described by Glass et al (Science 211, 70, 1980).

4) Specificity of the Organic Tissues

The specificity of the antibodies present in the myeloma supernatants and the ascite liquids were studied using indirect immunofluorescence on frozen sections of 4 μm in thickness as described by Bernard et al (Brit. J. Dermatol. 112, 647, 1985). Epithelial tissues of varied animal origins were used so as to study the specificity of each species, and the various epithelial tissues of human origin were used to study the specificity of the organic tissues. Human pathological tissues were also used to evaluate the diagnostic value of the present invention. This study related to the pathological skins of benign tumors, malignant tumors and dermatoses associated with anomalies of proliferation and keratinocytic differentiation.

5) Reactivity of the Antibodies with the Antigens with a Cellular Surface

When, during indirect immunofluorescence on a frozen section of nonpathological human skin, the labelling appears membranous, this localization was confirmed by immunolabelling using an electronic microscope employing the method of Graham and Karnovsky (J. Histochem. Cytochem. 14, 291, 1966), by immunolabelling of cells in culture, fixed with paraformaldehyde (PFA) diluted to 3% in PBS (Bernard et al, Cancer Res. 45, 1707, 1985), and by immunomarking on isolated cells by careful trypsination from human epidermis (Freeman et al, In Vitro 12, 352, 1976).

6) RESULTS

The antibody ($BC_5$) identified a protein of 62,000 daltons. This protein was detected after separation of the proteins from human epidermal cells by electrophoresis in polyacrylamide-SDS gel, and electrotransfer onto nitrocellulose. The immunofluorescence studies demonstrated the suprabasal localization of this antigen in the epidermis of man, monkey, horse, cow, goat, rabbit and mouse. The distribution of this antigen was highly altered in the papilloma and in the implied psoriasic epidermis. In the case of psoriasis, it only appeared in the upper nonproliferative zones. In the case of the papilloma it was absent from the lesions. It was also absent from the intestinal cells of base cell carcinoma and spinocellular carcinoma.

The labelling of human keratinocytes in primoculture fixed with methanol at $-20°$ C. or with PFA with permeabilization with Triton X-100 was cytoplasmic and diffused, which demonstrated that the antigen recognized by $BC_5$ was not associated with the cytoskeleton and was not a cytokeratin.

The results obtained are summarized in Tables I to III below:

TABLE I

SPECIES SPECIFICITY OF THE ANTIBODY SECRETED BY THE $BC_5$ CELL

| Species Tested[a] | | | | | | | |
|---|---|---|---|---|---|---|---|
| Mouse | Rabbit | Guinea Pig | Goat | Cow | Horse | Monkey | Man |
| +++ | ++ | +++ | + | ++ | ++ | ++ | +++ |

[a] by immunofluorescence on frozen sections of skin
+++ considerable labelling
++ less considerable labelling
+ weak labelling
− marking absent

TABLE II

SPECIFICITY OF THE ORGANIC TISSUE IN MAN OF THE ANTIBODY SECRETED BY $BC_5$

| Tissues Tested[a] | | | | | |
|---|---|---|---|---|---|
| Skin | Esophagus | Ureter | Stomach | Colon | Small Intestine |
| + | ++ | − | − | − | − |

[a] by immunofluorescence on frozen sections of skin

TABLE III

CUTANEOUS PATHOLOGY: ABSENCE OR PRESENCE OF THE ANTIGEN RECOGNIZED BY THE ANTIBODY SECRETED BY $BC_5$

| Melanoma (5)[a] | Naevus (2) | Base cell Carcinoma (4) | Carcinoma (4) |
|---|---|---|---|
| − | − | − | − to ± |

[a] The figure in parentheses represents the number of cases studied.

I claim:
1. A protein, characterized by the fact:
   that it is a nonkeratinic protein present in the cytoplasm of epidermal superbasal cells in man, the monkey, the horse, the cow, the mouse and the guinea pig, and to a lesser degree, in the goat;
   that it is absent in the following epithelial tissue of man: ureter, stomach, colon and small intestine, but is present in the esophagus;
   that it is absent in the following pathologically cells: basal cell carcinoma, melanoma and naevus;
   that it is decreased or absent in the following pathological cells: spinocellular carcinoma, psoriasis, papilloma;
   that it is immunologically bound by the antibody secreted by the hybrid cellular stock $BC_5$ deposited on Oct. 27, 1986 in the National Collection of Microorganisms of the Pasteur Institute under the No. I-615 under the EPC regulations, rules 28 and 28 bis; and
   that its molecular weight, measured by electrophoresis in polyacrylamide gel, is 62,000 daltons.
2. Antibodies characterized by the fact that they recognize an antigenic determinant of the protein of claim 1, said antibodies being either monoclonal antibodies or purified polyclonal antibodies.
3. The antibodies in accordance with claim 2, wherein said antibodies are secreted by the hybrid cellular stock $BC_5$.
4. The antibodies in accordance with claim 2 wherein said antibodies are antibodies which are labelled and fixed on a solid support or fixed on a solid support.
5. Hybrid cellular stocks that secrete an antibody as defined in claim 2.
6. A process for preparing hybrid cells that secrete an antibody that recognizes an antigenic determinant of the protein of claim 1 comprising immunizing an animal with said protein or with human keratinocytes, collect- ing the lymphocytes of the immunized animal, effecting a cellular fusion of myeloma cells cultivatable in vitro and selected clones secreting antibodies that recognize a cytoplasmic antigen of superabasal cells of the epidermis of man and other mammals defined in claim 1.

7. A process for preparing antibodies that recognize an antigenic determinant of the protein of claim 1 comprising cultivating hybrid cells that secret antibodies that recognize an antigenic determinant of said protein and separating the resulting antibodies.

* * * * *